United States Patent
Moilanen et al.

(10) Patent No.: US 6,733,463 B2
(45) Date of Patent: May 11, 2004

(54) METHOD AND MEASURING EQUIPMENT FOR MEASURING NITRIC OXIDE CONCENTRATION IN EXHALED AIR

(76) Inventors: Eeva Moilanen, Plysynkatu 11, FIN-33500 Tampere (FI); Lauri Lehtimäki, Insinoorikatu 58 A 11, FIN-33720 Tampere (FI)

(*) Notice: Subject to any disclaimer, the term of this patent is extended or adjusted under 35 U.S.C. 154(b) by 6 days.

(21) Appl. No.: 10/145,036

(22) Filed: May 15, 2002

(65) Prior Publication Data

US 2002/0193698 A1 Dec. 19, 2002

Related U.S. Application Data

(60) Provisional application No. 60/290,679, filed on May 15, 2001.

(51) Int. Cl.[7] .................................................. A61B 5/08
(52) U.S. Cl. ....................................... 600/532; 600/538
(58) Field of Search ................................. 600/529, 531, 600/532, 533, 537, 538, 539, 540, 541

(56) References Cited

U.S. PATENT DOCUMENTS 5,922,610 A 7/1999 Alving et al.
6,010,459 A * 1/2000 Silkoff et al. ................ 600/532
6,038,913 A * 3/2000 Gustafsson et al. .......... 73/23.3

FOREIGN PATENT DOCUMENTS

| DE | 195 45 794 A1 | 8/1997 |
| EP | FI/EP 0973444 | 1/2000 |
| WO | 97/38307 | 10/1997 |
| WO | 98/43539 | 10/1998 |
| WO | 01/82782 A2 | 11/2001 |

* cited by examiner

*Primary Examiner*—Max F. Hindenburg
*Assistant Examiner*—Navin Natnithithadha
(74) *Attorney, Agent, or Firm*—Young & Thompson

(57) ABSTRACT

A method for measuring nitric oxide concentration in exhaled air through a blow tube of a measuring equipment. The nitric oxide concentration is measured in the exhaled air flowing in the blow tube, a flow rate of the exhaled air flowing through the blow tube is measured during the exhalation and flow resistance of the blow tube is adjusted on the basis of the measured flow rate value such that the flow rate of the exhaled air substantially remains at a preset value. The method is used to diagnose an inflammatory lung disease in a patient whereby an increased nitric oxide concentration indicates an inflammatory lung disease, such as alveolitis.

15 Claims, 2 Drawing Sheets

METHOD AND MEASURING EQUIPMENT FOR MEASURING NITRIC OXIDE CONCENTRATION IN EXHALED AIR

FIELD OF THE INVENTION

The invention relates to a method for measuring nitric oxide (NO) concentration in exhaled air, in which method the exhaled air is blown through a blow tube in measuring equipment, and nitric oxide concentration is measured in the exhaled air flowing in the blow tube. Further, the invention relates to measuring equipment for measuring the nitric oxide concentration of exhaled air, the measuring equipment comprising a blow tube, through which the exhaled air is blown and a measuring means for measuring the nitric oxide concentration of the exhaled air flowing through the blow tube.

BACKGROUND OF THE INVENTION

Nitric oxide is a gaseous molecule that is intrinsically easily reactive. It also acts in the body as a signaling molecule that has various physiological and pathophysiological functions. For instance, nitric oxide regulates the function of respiratory organs in various conditions both in normal physiological and inflammatory states. Even though nitric oxide is easily reactive, some of the nitric oxide produced in the lungs mixes with pulmonary air and minor amounts of nitric oxide can be measured in exhaled air. In inflammatory lung diseases, such as asthma and alveolitis, the nitric oxide concentration of the exhaled air is higher than normal, since the nitric oxide concentration has increased because of the inflammation. So, the nitric oxide concentration can be used as an indicator of an inflammation in the lungs and of inflammatory diseases.

The nitric oxide concentration of exhaled air can be measured by an analyzer intended for that purpose. Currently, analyzers based on ozone chemiluminescence technology are commercially available on the market. In known measuring methods, a person to be examined exhales the exhalation air into an analyzer such that the flow rate of the exhaled air remains substantially constant. By this measuring method it is possible to detect a rise in the nitric oxide concentration of the exhaled air and thus to conclude, on the basis of the increased nitric oxide concentration, that there is inflammation in the lungs, but in which part of the lungs said inflammation is located cannot be found out by this method.

Mathematical models on pulmonary NO dynamics have been published during the past few years, in which models the lungs are divided into two compartments, i.e. a bronchial compartment and an alveolar compartment. On the basis of these models it is possible to calculate separately bronchial NO flux and correspondingly alveolar NO concentration. On the basis of these parameters, it is possible to assess in which lung compartment according to the model the nitric oxide production has increased and/or the nitric oxide diffusion has changed, and hence it can be determined relatively reliably, in which lung compartment according to the model inflammation may be located.

In known nitric oxide measuring devices a predetermined exhalation flow rate can be provided by devices with known flow resistance, and during the measurement, the aim is to keep the exhalation flow rate desired by keeping the exhalation pressure constant. In these known solutions the patient monitors the exhalation pressure value either with a separate pressure gauge or on the computer display and tries to keep the pressure at a predetermined pressure value as constant as possible during the whole exhalation. Another measuring method is to use a flow rate meter, whereby the person to be measured monitors the flow rate and attempts to keep it as steady as possible and at a predetermined value. The prior art has a problem that the result depends on the ability of the person to be measured to keep his/her exhalation flow rate constant by monitoring the exhalation pressure or exhalation flow rate on the display. A problem with this technique is that the nitric oxide concentration of exhaled air changes greatly as the exhalation flow rate changes, and thus even a slight error or minor variations in the exhalation flow rate cause a considerable error in the measurement result of nitric oxide concentration.

In connection with the measurement, it should also be taken into account that very large amounts of nitric oxide are produced in the nasal cavity and in paranasal sinuses as compared with lower airways. In order that the measurement of nitric oxide concentration in the lungs could be carried out reliably from the exhaled air blown through the mouth, it must be made sure that no considerable amounts of nitric-oxide-containing air from the nasal cavity can be mixed with the air blown out from the lungs. This can be achieved by exhaling against a minor pressure during the nitric oxide measurement, whereby the soft palate closes the connection between the nasopharynx and the oral cavity preventing the above-mentioned airs from being mixed together. This can be achieved by a counter pressure of about 5 cm $H_2O$.

The object of the present invention is to provide a method and measuring equipment, by which production and diffusion of nitric oxide in various parts of the lungs can be assessed more reliably and readily than before.

SUMMARY OF THE INVENTION

The method of the invention is characterized in that during exhalation the flow rate of the air flowing through a blow tube is measured and the flow resistance of the blow tube is adjusted on the basis of the measured flow rate value such that the flow rate of the exhaled air substantially remains at a predetermined flow rate value.

One preferred embodiment of the method according to the invention is characterized in that at least two different flow rate values are set for the exhaled air during the measurement, that the flow resistance of the blow tube is adjusted such that the flow rate of the exhaled air flowing through the blow tube sets in sequence either to one or more predetermined flow rates and that the nitric oxide concentration of the exhaled air is measured at each flow rate.

A second preferred embodiment of the method according to the invention is characterized in that the measured nitric oxide concentrations of the exhaled air are expressed proportional to the exhalation flow rate.

Measuring equipment of the invention, in turn, is characterized by comprising a flow sensor for measuring air flow rate and a flow resistance adjuster for adjusting the flow rate of exhaled air flowing through said tube to be substantially of predetermined magnitude during the measurement.

One preferred embodiment of the measuring equipment of the invention is characterized by comprising control means for setting the flow rate of exhaled air in sequence to at least two different flow rate values and for measuring the nitric oxide concentration from the exhaled air at each flow rate value during either one or more exhalations.

A second preferred embodiment of the measuring equipment of the invention is characterized in that the control means comprise a computer, to which are connected a measuring means for measuring the nitric oxide concentration and a flow meter, and which is correspondingly connected to control the flow adjuster for performing the measuring process preprogrammed in the computer on the basis of the preset air flow rate values.

A third preferred embodiment of the measuring equipment of the invention is characterized in that the flow meter is a mass flow meter and the flow adjuster is a mechanical, electrically controlled throttle.

The basic idea of the invention is that, during exhalation, exhalation flow rate is measured and controlled such that the flow rate remains substantially at a predetermined value while nitric oxide concentration of the air flowing out at said predetermined flow rate is measured. Further, the basic idea of the invention is that the air flow exhaled through the blow tube of the measuring equipment is adjusted by setting a plurality of different, predetermined flow rate values for it and the nitric oxide concentration of the exhaled air is measured at each preset flow rate value. According to one preferred embodiment of the invention, both the air flow rate adjustment and the nitric oxide concentration measurement at each set value are performed automatically during one or more exhalations.

BRIEF DESCRIPTION OF THE DRAWINGS

The invention will be described in greater detail with reference to the attached drawings, wherein.

DETAILED DESCRIPTION OF THE INVENTION

Figure 1:
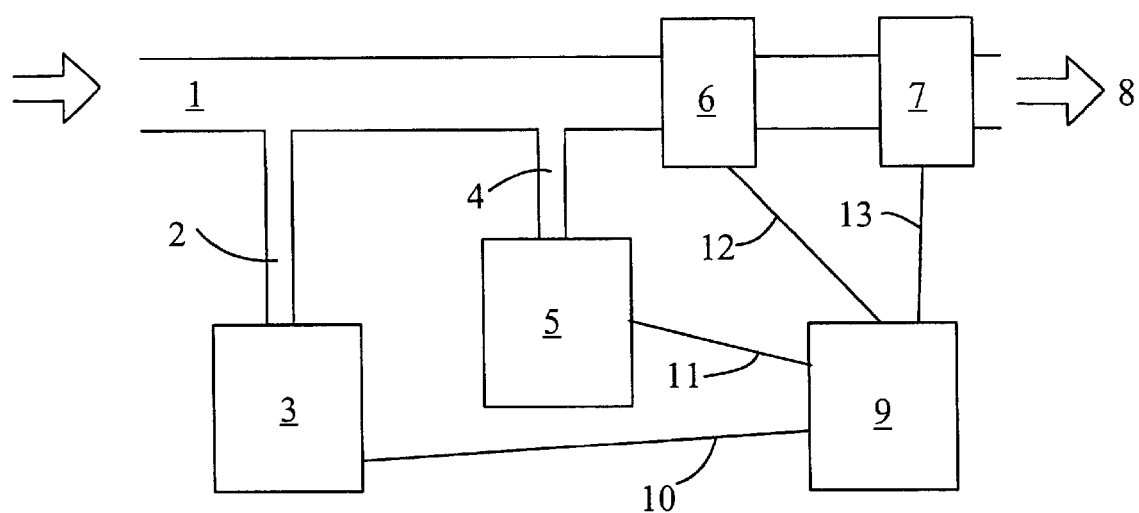
FIG. 1 is a schematic view of equipment according to the invention.

FIG. 1 shows schematically measuring equipment according to the invention for measuring nitric oxide concentration of exhaled air. The measuring equipment comprises a blow tube 1, into which the person to be measured blows his/her exhalation air. There is a measuring channel 2 from the blow tube 1 to an NO analyzer 3 acting as a measuring means, which measures the nitric oxide concentration of the exhaled air. The amount of sample air passing into the NO analyzer 3 in a time unit remains constant at a sufficient accuracy irrespective of the exhalation pressure by means of the flow resistance therein.

The majority of the exhaled air is supplied forwards, and the blow tube 1 is connected through a pressure tube 4 to a pressure gauge 5, which indicates the pressure prevailing in the blow tube. The exhaled air flows further to a flow meter 6 and therefrom further through a flow rate adjuster 7 to free ambient air 8. The flow meter 6 can be a complete meter with all necessary measuring means and sensors as well as components intended for processing the measurement results, or a simpler device, for instance an air flow measuring sensor, whose measurement signal can be processed in another device, such as a computer. Correspondingly, the flow rate adjuster is in principle an element that regulates the flow resistance of the blow tube, for instance a throttle. By adjusting the flow resistance it is possible to control the flow rate through the blow tube. The flow meter 6 allows to measure the flow rate of exhaled air flowing therethrough, and correspondingly, the flow rate adjuster 7 allows to adjust flow resistance, i.e. throttling. The measuring equipment also comprises control means, such as a computer 9, to which the NO analyzer 3, the pressure gauge 5, the flow meter 6 and the flow rate adjuster 7 can be connected by signal and/or control channels 10 to 13.

The NO analyzer 3 is connected to the computer 9 by a signal channel 10, through which information on measured NO concentration is transferred to the computer in a suitable form. The pressure gauge 5, which can be either a separate pressure gauge or a mere pressure sensor, is in turn connected to the computer 9 by a signal channel 11, along which information on the pressure prevailing in the blow tube 1 is transferred to the computer in a suitable form. This pressure value is mainly informative, because the pressure range that is useful during blowing is relatively large depending on the characteristics of the equipment. However, it indicates whether the blow pressure is within a suitable range (cf. limit value above) and gives the person to be measured an opportunity to control his/her blowing if the pressure tends to shift towards either edge of the measuring range. The flow meter 6, in turn, is connected to the computer by a signal channel 12. The flow meter 6 measures the flow rate of the exhaled air and provides, in a suitable form, the computer 9 with information on the flow rate via the signal channel 12, on the basis of which information the computer 9 can adjust the flow rate adjuster 7 by means of the control channel 13. When a predetermined flow rate value is programmed into the computer 9, it adjusts the flow rate adjuster 7 on the basis of the value obtained from the flow meter 6, when necessary, such that as the flow rate decreases, the throttle in the flow tube is reduced by the flow rate adjuster 7, and correspondingly, as the flow rate rises the throttle in the tube is increased, and as a consequence the flow rate increases or decreases respectively, i.e. becomes towards the set value.

FIG. 1 shows one sequence for various parts of the measuring equipment. Naturally, they can also be coupled in another order with respect to each other, with the proviso that the operational preconditions remain. Thus, the flow meter 6, the pressure gauge 5 and the nitric oxide analyzer 3 can be mounted to be in a suitable mutual order in view of the practical use.

According to one preferred embodiment, as the method of the invention is applied the person to be measured blows exhaled air through a tight mouthpiece to a blow tube 1. Prior to the measuring session, the computer 9 is programmed to set the flow rate in the blow tube 1 to one or more predetermined flow rate values consecutively. As the measuring starts, the computer sets the flow rate to the first predetermined flow rate value and the nitric oxide concentration of exhaled air is measured at this flow rate. Thereafter, if there are several measurement values, the computer takes into use the next preset air flow rate and measures the nitric oxide concentration at that flow rate, etc., until the nitric oxide concentration is measured at all preset flow rate values. In connection with the measuring session, the computer stores both the flow rate values and the measured nitric oxide concentrations in a memory for processing them in a manner or for printing them out as such. In practice, the measurement takes place during one or more exhalations without any components in the measuring equipment needing to be changed in any way.

The measuring equipment of the invention can be implemented in a variety of different ways. The measuring equipment can be implemented e.g. by constructing a separate flow control unit and by connecting it to a separate NO analyzer. Correspondingly, in this connection it is possible to use a conventional computer that is connected in a suitable manner, such as by electric wires, optical cables or wireless channels to various components of the measuring equipment for receiving and controlling the measurement results respectively. It is also possible to construct a completely compact measuring unit which includes the necessary components, and instead of a powerful desktop computer or the like, a small, possibly simple control unit which is capable of controlling the air flow rate and storing the measurement results in a memory. In this implementation, the control unit belonging to the control means need not necessarily be capable of processing the measurement results in any way. It is also possible to construct measuring equipment which has a separate measuring device that is provided with wireless data transmission technology known per se or the like, such that the measuring device per se can be a fully wireless compact entity cooperating with a separate computer or the like by using an installed program.

The flow meter 6 can be any flow rate meter known per se, such as a mass flow meter. Correspondingly, the flow rate adjuster can be any throttle known per se, however, preferably a mechanical throttle that is electrically controlled such that it can be adjusted by means of an electrically operating control unit.

Figure 2:
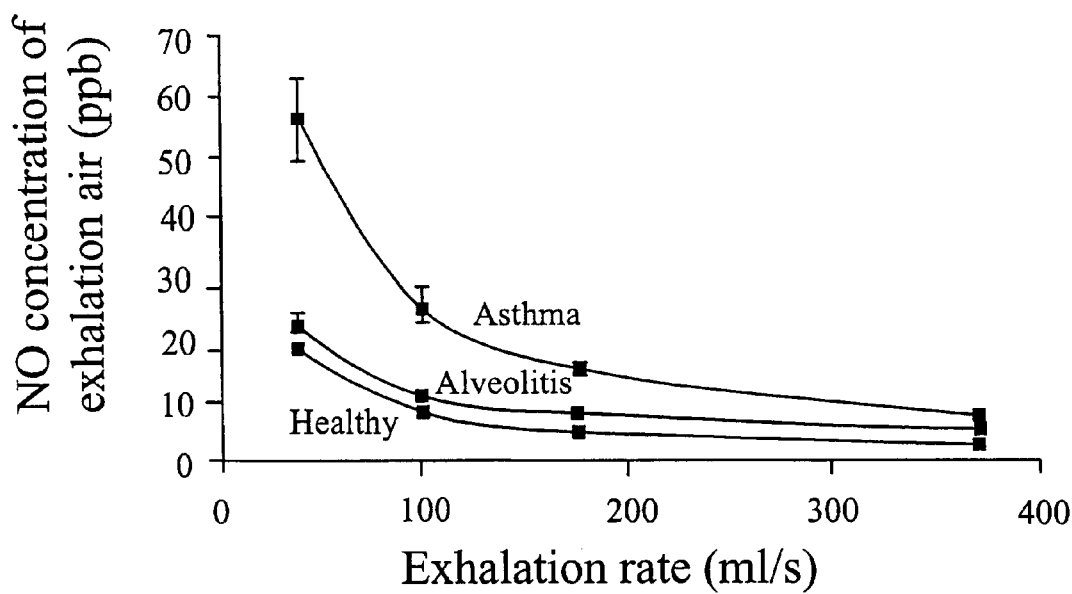
FIG. 2 is a schematic diagram of NO concentration of exhaled air measured at four different exhalation flow rates from a test group.

FIG. 2 shows nitric oxide concentration of exhaled air at four different exhalation flow rates (40, 100, 175 and 370 ml/s). The different exhalation flow rates were obtained by changing the known mechanical flow resistance in the exhalation tube for each exhalation flow rate. The test person has monitored the exhalation pressure in the pressure gauge and the desired exhalation flow rate has been achieved by keeping the exhalation pressure at a predetermined level. The measured groups were 40 patients with asthma, 17 patients with alveolitis and 57 healthy reference persons. The figure shows the dependence of exhaled NO concentration on the exhalation flow rate for these test persons. The alveolar NO concentration and bronchial NO flux of each test person can be calculated from the measurement results. The bronchial NO flux of the patients with asthma is higher than that of the healthy persons or the patients with alveolitis because of bronchial inflammation. The patients with alveolitis suffering from alveolar inflammation have, in turn, higher alveolar NO concentration than healthy persons or asthmatics.

Figure 3:
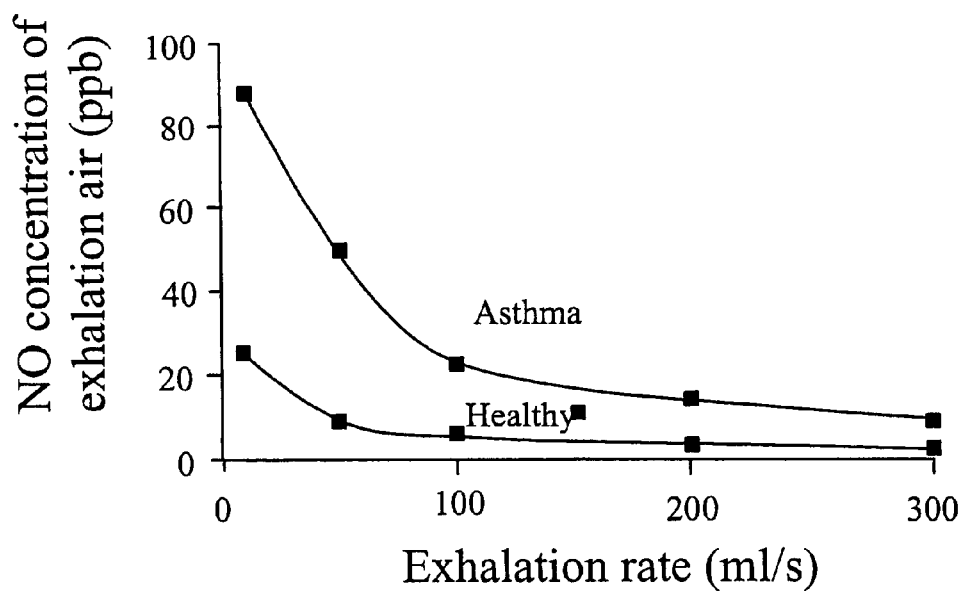
FIG. 3 is a schematic diagram of NO concentration as a function of exhalation flow rate measured from a second test group.

FIG. 3 shows the nitric oxide concentration of exhaled air of one healthy child and one child with asthma at five different exhalation flow rates (10, 50, 100, 200 and 300 ml/s). The measurements at different exhalation flow rates have been carried out by using the device according to the invention. The alveolar NO concentration and the bronchial NO flux of both test persons can further be calculated from the measurements. Because very low exhalation flow rates have also been used in the measurements, it is possible to calculate, in addition to the above-mentioned variables, the nitric oxide concentration of the bronchial wall tissue and the NO diffusion capacity in said tissue. On the basis of these calculated variables, it is possible to draw conclusions on the intensity and location of the inflammation in the lungs in the same manner as in the material of FIG. 2.

The method and equipment of the invention can be employed for measuring the nitric oxide concentration of exhaled air reliably and effectively, and by means of them it is also possible to obtain clear and reliable descriptors of nitric oxide concentration at different exhalation flow rates, on the basis of which a possible inflammation in the lungs and its location can be detected on a preliminary basis.

During the preliminary year we have published experimental data supporting the role of the present (multiple exhalation flow) method in diagnosis and follow-up of treatment of inflammatory lung diseases. We measured exhaled NO concentration at three different exhalation flow rates (100, 175 and 370 mL/s) in 17 patients with alveolitis (alveolar inflammation), in 40 patients with asthma (bronchial inflammation) and in 57 age-matched and sex-matched healthy controls. Based on these measurements alveolar NO concentration and bronchial NO flux were calculated to each subject according to the previously mentioned mathematical model by Tsoukias and George. We found that patients with alveolitis had normal bronchial NO flux but 3.7 times higher alveolar NO concentration as compared with healthy controls. Patients with asthma had normal alveolar NO concentration but 3.6 times higher bronchial NO flux as compared with healthy controls.

We also studied the effect of anti-inflammatory drug treatment on alveolar and bronchial NO output in patients with asthma and alveolitis. 16 patients with asthma started 8 weeks of treatment with inhaled glucocorticoids to suppress their asthmatic airway inflammation. The treatment had no effect on alveolar NO concentration, which was normal already before the treatment. However, there was a significant decrease in bronchial NO flux already after one week of anti-inflammatory treatment, and after 8 weeks the bronchial NO flux of these 16 asthmatics was similar to healthy controls. The decrease in bronchial NO flux during the drug treatment took place simultaneously with decrease in asthmatic symptoms and improvement of lung function of these subjects. 7 patients with alveolitis were treated with anti-inflammatory drugs or they avoided exposure to the allergen causing their disease for two months. Alveolar NO concentration decreased significantly during the treatment while lung function was improved. There was no change in bronchial NO flux during the treatment.

These results support the role of present invention in differential diagnosis of alveolar and bronchial inflammatory diseases. The results also suggest that the present method can be used to follow-up drug treatment of inflammatory lung diseases and provide means to assess the efficacy of such treatment.

References

American Thoracic Society. Recommendations for standardized procedures for the online and offline measurement of exhaled lower respiratory nitric oxide and nasal oxide in adults and children. *Am. J. Respir. Crit. Care Med.* 160, 2104–2117.

Gustafsson L E, Leone A M, Persson M G, Wiklund N P and Moncada S. Endogenous nitric oxide is present in the exhaled air of rabbits, guinea pigs and humans. *Biochem Biophys Res Commun* 1991; 181: 852–857.

Kharitonov S, Alving K, Barnes P J. Exhaled and nasal nitrix oxide measurements: rekommendations. The European Respiratory Society Task Force. *Eur Respir J* 1997; 10: 1683–1693.

Kharitonov S A, Yates D, Robbins R A, Logan-Sinclair R, Shinebourne E A, Barnes P J. Increased nitric oxide in exhaled air of asthmatic patients. *Lancet* 1994: 343: 133–135.

Kharitonov S A, Barnes P J. Nasal contribution to exhaled nitric oxide during exhalation against resistance or during breath holding. *Thorax* 1997; 52: 540–544.

Lehtimäki L, Turjanmaa V, Kankaanranta H, Saarelainen S, Hahtola P, Moilanen E. Increased bronchial nitric oxide production in patients with asthma measured with a novel method of different exhalation flow rates. *Ann Med* 2000; 32: 417–423.

Lehtimäki L, Kankaanranta H, Saarelainen S, Hahtola P, Järvenpää R, Koivula T, Turjanmaa V, Moilanen E. Extended exhaled NO measurement differentiates between alveolar and bronchial inflammation. *Am J Respir Crit Care Med* 2001; 163: 1557–1561.

Lehtimäki L, Kankaanranta H, Saarelainen S, Turjanmaa V, Moilanen E. Inhaled fluticasone decreases bronchial but not alveolar nitric oxide output in asthma. *Eur Respir J* 2001; 18: 635–639.

Paredi P, Kharitonov S A, Loukides S, Pantelidis P, du Bois R M, Barnes P J. Exhaled nitric oxide is increased in active fibrosing alveolitis. *Chest* 1999; 115: 1352–1356.

Pietrapaoli A P, Perillo I B, Torres A, Perkins P T, Frasier L M, Utell M J, Frampton M W, Hyde R W. Simultaneous measurement of nitric oxide production by conducting and alveolar airways of humans. *J Appl Physiol* 1999; 87: 1532–1542.

Silkoff P E, Sylvester J T, Zamel N, Parmutt S. Airway nitric oxide diffusion in asthma: Role in pulmonary function and bronchial responsiveness. *Am J Respir Crit Care Med* 2000; 161: 1218–1228.

Tsoukias N M, George S C. A two-compartment model of pulmonary nitric oxide exchange dynamics. *J Appl Physiol* 1998; 85: 653–666.

What is claimed is:

1. A method for measuring nitric oxide concentration in exhaled air, comprising the steps of:
   exhaling air through a blow tube of measuring equipment, and
   measuring the nitric oxide concentration in the exhaled air flowing in the blow tube, wherein,
   during the measuring step, a flow rate of the exhaled air flowing through the blow tube is measured to determine a measured flow rate value, and flow resistance of the blow tube is adjusted on the basis of the measured flow rate value such that the flow rate of the exhaled air substantially remains at a preset value.

2. The method as claimed in claim 1, wherein at least two different flow rate values are set for the flow rate of exhaled air during the measurement, and the flow resistance of the blow tube is adjusted such that the flow rate of the exhaled air flowing through the blow tube sets in sequence either to one or more predetermined flow rate values, and the nitric oxide concentration of the exhaled air is measured at each flow rate.

3. The method as claimed in claim 2, wherein the measured nitric oxide concentrations of exhaled air are expressed proportional to the exhalation flow rate.

4. Measuring equipment for measuring nitric oxide concentration, the measuring equipment comprising:
   a blow tube, through which exhaled air is blown; and
   a measuring means for measuring the nitric oxide concentration of the exhaled air flowing through the blow tube, the measuring equipment further comprising
   a flow meter for measuring air flow rate and
   a flow rate adjuster for adjusting the flow rate of exhaled air flowing through said tube to be substantially predetermined in magnitude during the measurement of nitric oxide concentration.

5. The measuring equipment as claimed in claim 4, comprising control means for
   i) setting the flow rate of the exhaled air consecutively to at least two different flow rate values and
   ii) measuring the nitric oxide concentration in the exhaled air at each flow rate value during either one or more exhalations.

6. The measuring equipment as claimed in claim 4, wherein the control means comprise a computer, to which are connected the measuring means for measuring the nitric oxide concentration and the flow meter, and which is correspondingly connected to control the flow rate adjuster for executing a measuring process preprogrammed in the computer on the basis of preset air flow rate values.

7. The measuring equipment as claimed in claim 5, wherein the control means comprise a computer, to which are connected the measuring means for measuring the nitric oxide concentration and the flow meter, and which is correspondingly connected to control the flow rate adjuster for executing a measuring process preprogrammed in the computer on the basis of preset air flow rate values.

8. The measuring equipment as claimed in claim 4, wherein the flow meter is a mass flow meter and the flow rate adjuster is a mechanical, electrically controlled throttle.

9. The measuring equipment as claimed in claim 5, wherein the flow meter is a mass flow meter and the flow rate adjuster is a mechanical, electrically controlled throttle.

10. The measuring equipment as claimed in claim 6, wherein the flow meter is a mass flow meter and the flow rate adjuster is a mechanical, electrically controlled throttle.

11. Method of diagnosing an inflammatory lung disease in a patient comprising: measuring nitric oxide concentration in exhaled air of said patient, whereby the air is exhaled through a blow tube of measuring equipment, and the nitric oxide concentration is measured in the exhaled air flowing in the blow tube, wherein a flow rate of the exhaled air flowing through the blow tube is measured during the exhalation and flow resistance of the blow tube is adjusted on the basis of the measured flow rate value such that the flow rate of the exhaled air substantially remains at a preset value, whereby an increased nitric oxide concentration indicates an inflammatory lung disease.

12. Method as claimed in claim 11, wherein at least two different flow rate values are set for the flow rate of exhaled air during the measurement, and the flow resistance of the blow tube is adjusted such that the flow rate of the exhaled air flowing through the blow tube sets in sequence to said predetermined flow rate values, and the nitric oxide concentration of the exhaled air is measured at each flow rate, on the basis of which the location of a possible inflammation can be calculated.

13. Method as claimed in claim 12, wherein the alveolar NO concentration and the bronchial NO flux is calculated, whereby an increase in the alveolar NO concentration indicates alveolar or parenchymal lung inflammation, and an increase in the bronchial NO flux indicates bronchial lung inflammation.

14. Method of monitoring the effect of anti-inflammatory drug treatment in a patient in need thereof comprising: measuring nitric oxide concentration in exhaled air of said patient, whereby the air is exhaled through a blow tube of measuring equipment, and the nitric oxide concentration is measured in the exhaled air flowing in the blow tube, wherein a flow rate of the exhaled air flowing through the blow tube is measured during the exhalation and flow resistance of the blow tube is adjusted on the basis of the measured flow rate value such that the flow rate of the exhaled air substantially remains at a preset value, whereby a decrease in nitric oxide concentration indicates an effect of the anti-inflammatory drug treatment on an inflammatory lung disease in said patient.

15. Method as claimed in claim 14, wherein at least two different flow rate values are set for the flow rate of exhaled air during the measurement, and the flow resistance of the blow tube is adjusted such that the flow rate of the exhaled air flowing through the blow tube sets in sequence to said predetermined flow rate values, and the nitric oxide concentration of the exhaled air is measured at each flow rate, on the basis of which the alveolar NO concentration and the bronchial NO flux is calculated, whereby a decrease in the alveolar NO concentration indicates an effect of said anti-inflammatory drug treatment on alveolar or parenchymal lung inflammation, and a decrease in the bronchial NO flux indicates an effect of said anti-inflammatory drug treatment on bronchial lung inflammation.

* * * * *